Figure 1:
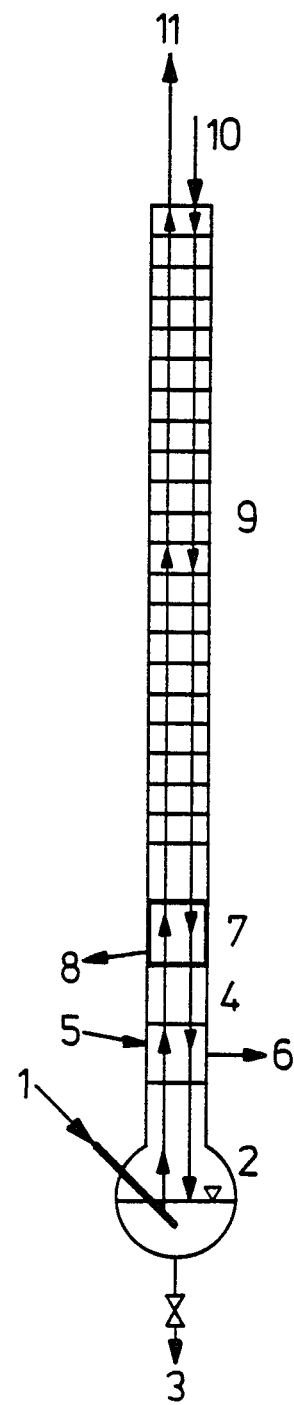

United States Patent [19]

Schnabel et al.

[11] Patent Number: 4,562,283

[45] Date of Patent: Dec. 31, 1985

[54] CONTINUOUS SEPARATION OF MALEIC ANHYDRIDE FROM GASEOUS REACTION MIXTURES

[75] Inventors: Rolf Schnabel, Schifferstadt; Hans M. Weitz, Bad Durkheim, both of Fed. Rep. of Germany

[73] Assignee: BASF Aktiengesellschaft, Ludwigshafen, Fed. Rep. of Germany

[21] Appl. No.: 681,593

[22] Filed: Dec. 14, 1984

[30] Foreign Application Priority Data

Dec. 21, 1983 [DE] Fed. Rep. of Germany ....... 3346134

[51] Int. Cl.⁴ .............................................. C07C 67/08
[52] U.S. Cl. ................................... 560/204; 549/257; 549/258; 549/262; 562/595; 568/864
[58] Field of Search ......................... 560/204; 562/595; 549/257, 258, 262; 568/864

[56] References Cited

U.S. PATENT DOCUMENTS

| 3,830,830 | 8/1974 | Cleveland et al. | 560/204 |
| 3,875,210 | 4/1975 | Golembeski | 560/204 X |
| 3,923,881 | 12/1975 | Murib et al. | 560/204 X |
| 3,979,443 | 9/1976 | Schwartz et al. | 560/204 |
| 4,032,458 | 6/1977 | Cooley et al. | 568/864 |
| 4,268,695 | 5/1981 | Lange et al. | 568/864 |
| 4,361,710 | 11/1982 | Weitz et al. | 568/864 |

FOREIGN PATENT DOCUMENTS

| 2543673 | 4/1976 | Fed. Rep. of Germany . |
| 2845905 | 4/1980 | Fed. Rep. of Germany . |
| 3106819 | 9/1982 | Fed. Rep. of Germany . |
| 1454440 | 11/1976 | United Kingdom . |

*Primary Examiner*—James H. Reamer
*Assistant Examiner*—Vera C. Clarke
*Attorney, Agent, or Firm*—John H. Shurtleff

[57] ABSTRACT

Maleic anhydride is separated off from gaseous reaction mixtures by a continuous process in which the gaseous reaction mixture containing the maleic anhydride is brought into contact with butanol, the gaseous substances obtained in this procedure are brought into contact with butyl maleate by a countercurrent method, and the liquid product is removed from the bottom.

2 Claims, 2 Drawing Figures

CONTINUOUS SEPARATION OF MALEIC ANHYDRIDE FROM GASEOUS REACTION MIXTURES

The present invention relates to a process for the continuous separation of maleic anhydride (MA) from gaseous reaction mixtures.

German Laid-Open Application DOS 2,543,673 discloses that butane-1,4-diol can be prepared from MA if, in a first stage, MA is esterified with n-butanol and, in a second stage, the dibutyl maleate is hydrogenated catalytically. In a process described in German Pat. No. 2,845,905, butane-1,4-diol is produced in a single stage, wherein a mixture of MA and the alcohol is subjected directly to catalytic hydrogenation, complete esterification of MA being dispensed with.

German Laid-open Application DAS 3,106,819 proposes separating MA from a gaseous reaction mixture by washing with butane-1,4-diol. The mixture obtainable in this procedure is hydrogenated to butane-1,4-diol. Although in this procedure no solvent has to be separated off, it is not possible to obtain high concentrations of MA or of monomeric MA secondary products in the absorbate as well as to prevent the formation of undesirable oligomers and polymers of butanediol and MA. However, both of these are desirable, since high space-time yields can be achieved only with high absorbate concentrations, and oligomers and polymers have an adverse effect on the catalyst in the subsequent hydrogenation step.

If an attempt is made to obtain mixtures of butanol and MA, which are suitable for the preparation of butanediol, by washing reaction gases containing gaseous MA with butanol, the high butanol content of the waste gas gives rise to such considerable technical difficulties that it is impossible to operate a butanol wash economically.

It is an object of the present invention to provide a process for washing MA out of reaction gases with solvents which gives, in a very economical manner, a liquid mixture which can advantageously be hydrogenated to obtain butane-1,4-diol.

We have found that this object is achieved by the process according to the invention, in which the continuous separation of MA from gaseous reaction mixtures obtained by catalytic oxidation of hydrocarbons at from 250° to 600° C. is carried out by treating the gaseous reaction mixture with a solvent by a method in which the MA-containing gaseous reaction mixture is cooled to 50°–200° C. and brought into contact with butanol, the resulting gaseous substances are brought into contact with dibutyl maleate by a countercurrent procedure, and the liquid product containing butyl maleate is removed from the bottom.

In the novel process, an MA-containing gaseous reaction mixture is brought into contact with butanol in order to absorb MA. Suitable butanols are isobutanol and n-butanol, the latter preferably being used as the absorbent. In an advantageous embodiment of the process, the reaction gas is fed in below the surface of the liquid butanol, for example through a dip tube. However, the reaction mixture can also be passed into an absorption column directly from below, liquid butanol flowing countercurrent to the said mixture in the column. The procedure in which the MA absorption is carried out in a column or in a plurality of columns connected in succession is preferred. The reaction mixture may also be brought into contact with gaseous butanol.

MA-containing reaction mixtures are obtained, for example, by the conventional catalytic oxidation of hydrocarbons, such as butenes, butane or benzene. In this conventional oxidation process, the gaseous reaction mixture flowing out of the reactor at from 250° to 600° C. contains 80 g/m$^3$ (S.T.P.) of maleic anhydride. The gaseous reaction mixtures also contain unconverted hydrocarbon, water, carbon monoxide, carbon dioxide, nitrogen and residual oxygen.

Examples of suitable columns are absorption columns, such as bubble cap, packed and sieve tray columns containing from 1 to 50, preferably from 5 to 20, trays. The procedure is advantageously carried out in such a way that the MA-containing gaseous reaction mixture is passed into the bottom of the column, butanol is fed into the lower part of the column, advantageously above the bottom, and the dibutyl maleate is passed into the column via the top. The temperature in the bottom is from 0° to 280° C., that in the column from 0° to 118° C., and that at the top of the column from 0° to 100° C.

From 0.2 to 10 moles of butanol and from 0.2 to 20 moles of dibutyl maleate are used per mole of MA in the gaseous starting mixture.

In a preferred procedure, in which the continuous separation of the MA is carried out in a column, the gas mixture and the butanol are, as described, passed into the bottom and into the lower part of the column, respectively. The lower part of the column is the part extending from above the bottom up to the second to fifth tray.

Any second liquid phase which may be present, and which mainly consists of water, is removed from the column above the feed point for the butanol, ie. above the second to fifth tray. A liquid mixture is removed from the middle part of the column, which is the region up to five trays above the take-off points for the aqueous phase; from the said liquid mixture, in a separate distillation apparatus, such as a distillation column, the fractions which are lower boiling than dibutyl maleate (bp. 267° C.) are distilled off and recycled to the lower part of the column. The dibutyl maleate obtained as a bottom product in this separate distillation is fed to the absorption column via the top. The column is operated so that the temperature at the lowest tray is from 25° to 118° C., preferably from 65° to 100° C., that in the middle part of the column is from 0° to 65° C., preferably from 25° to 65° C., and that at the top of the column is from 0° to 50° C., preferably from 0° to 30° C.

Under the conditions of the absorption according to the invention, the MA is predominantly converted to monobutyl and dibutyl maleate in the column. The gaseous substances which accompany the MA are removed via the top of the column, and some of the water may leave the column through the side take-off point. The liquid product which is removed from the lower part of the bottom of the column has, for example, the following composition: from 0.01 to 93% by weight of butanol, from 0.7 to 79% by weight of monobutyl maleate, from 5 to 99% by weight of dibutyl maleate and not more than 50% by weight of MA, maleic acid and fumaric acid. The dibutyl maleate usually contains substantial amounts of the isomeric compound butyl fumarate. The liquid mixture is very suitable for hydrogenation to produce butane-1,4-diol. In this connection, it is preferable to heat the liquid mixture to, for example, 100°–220° C. in order to complete the esterification, the water of reaction being expelled with the butanol, and the butanol required for the novel process thus being recovered. The dibutyl maleate can then be hydrogenated in a conventional manner to give butane-1,4-diol.

The novel process permits the MA from the reaction gases to be converted quantitatively, and substantially without loss of absorbent, to a liquid mixture which has a high concentration of the half-ester and diester of maleic acid and which is very suitable for hydrogenation to produce butane-1,4-diol. Surprisingly, troublesome deposition of crystals of maleic acid and/or fumaric acid does not take place in the procedure according to the invention.

Figure 2:
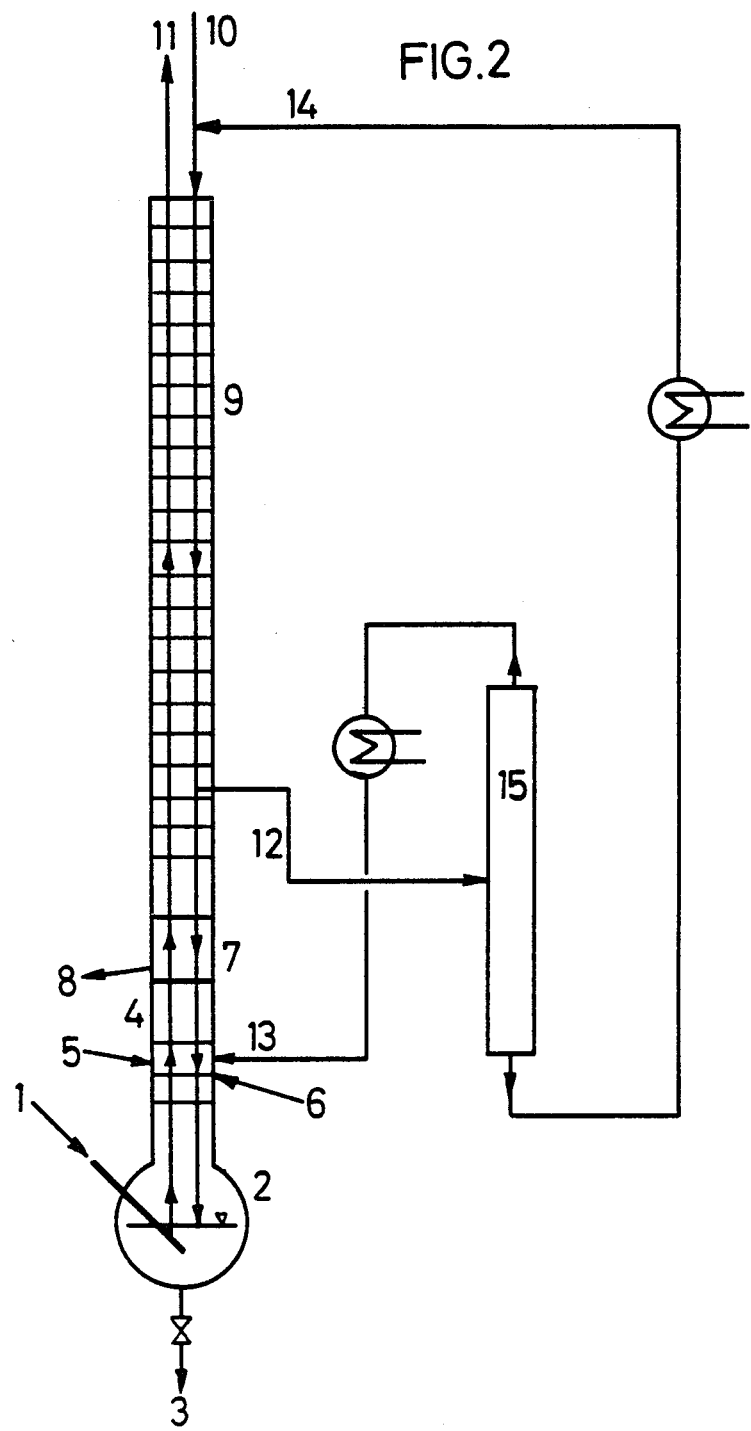

The invention is illustrated by the following examples to be considered together with the accompanying drawings wherein:

FIG. 1 is a schematic illustration of a flask equipped overhead with a multi-tray bubble cap column as used in Examples 1 and 2 below; and FIG. 2 is a schematic illustration in flowsheet form, similar to FIG. 1 but with the addition of a Sambay distillation unit being fed by liquid absorbate withdrawn from the bubble cap column and having top and bottom recycle streams which are cooled and returned to the bottom and top of the bubble cap column, respectively, all as used in Example 3 below.

EXAMPLE 1 (cf. FIG. 1)

A stream of 200 liters (S.T.P)/h of nitrogen is laden with MA and steam in a saturation vessel so that the stream contains 1 vol. % of MA and 5 vol. % of water. With regard to these components, the gas stream prepared in this manner substantially corresponds to a gaseous reaction mixture obtained in the conventional oxidation of butane, butenes or benzene with air in order to produce MA.

The gas mixture (1) is passed, at 75° C., into a flask (2) charged with ½ liter of butanol at the beginning of the experiment, the said gas mixture being introduced under the surface of the butanol. Liquid reaction mixture is removed from the flask through an outlet (3) at regular intervals so that the liquid level in the flask remains constant.

A section of a bubble cap column (4), which has 3 bubble trays and is equipped with a feed line (5) and a nozzle (6) for removing samples, is mounted on the flask. The temperature is kept at 60° C. in this part of the column.

10 ml/h of n-butanol are fed in via the feed line (5). On top of the column section (4) is a phase separator (7) which is provided with an outlet nozzle (8) and kept at 25° C. and through which any second liquid phase which may occur, and which has a higher density (aqueous phase), can be removed from the column. Further sections comprising a total of 21 bubble trays (9) are mounted above the phase separator (7), these sections being kept at 25° C.

20 ml/h of dibutyl maleate are fed in (10) via the top of the column, while at the same time a gas stream leaves the top of the column (11).

After an experimental time of 4 days, a steady state is established, and the following results are obtained. The MA fed in in gaseous form (10 g/h) is recovered, predominantly in the form of the esters, in the liquid mixture which collects in the lower part of the apparatus. Analysis of the mixture (3) discharged from the flask by gas chromatography and HPLC gives the following composition: 18.0% by weight of n-butanol, 31.0% by weight of monobutyl maleate, 46.4% by weight of dibutyl maleate and 4% by weight of MA, maleic acid and fumaric acid. At as low a point as the outlet nozzle (6), no MA, maleic acid, fumaric acid or half-esters are detectable. At the phase separator (7), 4–5 g/h of an aqueous phase containing from 7 to 8% by weight of n-butanol are separated off. In the upper part of the column (9), the n-butanol concentration decreases to 0.4%. 0.42 g/h of n-butanol, 0.04 g/h of dibutyl maleate and 5 g/h of water are discharged together with the waste gas (11).

EXAMPLE 2 (Comparative experiment)

The procedure described in Example 1 is followed, except that the butanol feed is dispensed with. Maleic acid crystallizes out in the column in the course of one day, so that the absorption has to be terminated. If, in the experiment, the dibutyl maleate feed is increased to about 100 ml/h, troublesome crystallization can be prevented but the resulting liquid product would require an additional concentration stage before being used for hydrogenation to produce butane-1,4-diol.

EXAMPLE 3 (cf. FIG. 2)

A stream of 200 liters (S.T.P.)/h of nitrogen is laden with MA and steam in a saturation vessel so that the stream contains 1 vol. % of MA and 5 vol. % of water. The gas stream prepared in this manner corresponds to a gaseous reaction mixture obtained in the conventional oxidation of butane, butenes or benzene with air in order to produce MA.

The gas mixture (1) is passed, at 100° C., into a flask (2) charged with ½ liter of butanol at the beginning of the experiment, the said gas mixture being introduced under the surface of the butanol. Liquid reaction mixture is removed from the flask through an outlet (3) at regular intervals so that the liquid level in the flask remains constant.

A section of a bubble cap column (4), which has 3 bubble trays and is equipped with a feed line (5) and a nozzle (6) for removing samples, is mounted on the flask. The temperature is kept at 65° C. in this part of the column.

20 ml/h of n-butanol are fed in via the feed line (5). On top of the column section (4) is a phase separator (7) which is provided with an outlet nozzle (8) and kept at 30° C. and through which any second liquid phase which may occur, and which has a higher density (aqueous phase), can be removed from the column. Further sections comprising a total of 21 bubble trays (9) are mounted above the phase separator (7), these sections being kept at 30° C.

An outlet nozzle is installed three trays above the phase separator (7), the liquid absorbate (12) being removed from the column section above this nozzle, via the said nozzle, and being fed to the distillation apparatus (15).

100 ml/h of dibutyl maleate are fed in (10,14) via the top of the column, while at the same time a gas stream leaves the top of the column (11).

After an experimental time of 4 days, a steady state is established, and the following results are obtained. The MA fed in in gaseous form (10 g/h) is recovered, predominantly in the form of the esters, in the liquid mixture which collects in the lower part of the apparatus. Analysis of the mixture (3) discharged from the flask by gas chromatography and HPLC gives the following composition: 25% by weight of n-butanol, 45% by weight of monobutyl maleate, 29% by weight of dibutyl maleate and 1% by weight of MA, maleic acid and fumaric acid. At as low a point as the outlet nozzle (6), no MA, maleic acid, fumaric acid or half-esters are detectable. At the phase separator (7), 4–5 g/h of an aqueous phase containing from 4 to 5% by weight of n-butanol are separated off. In the upper part of the column (9), the n-butanol concentration decreases to less than 0.1%. 0.008 g/h of n-butanol, 0.04 g/h of dibutyl maleate and 5–6 g/h of water are discharged together with the waste gas (11).

The absorbate (12) contains 0.8% by weight of water and 5.5% by weight of butanol. It is fed to a Sambay distillation (15), where butanol and water are separated from dibutyl maleate under 20 mbar and at 140° C. About 90 g/h of dibutyl maleate (14), which still contains 0.05% by weight of butanol, are fed to the top of the column, while the 16 g/h of top product (13), which contains 37% by weight of butanol, 5% by weight of water and 50% by weight of dibutyl maleate, are passed into the second tray of the absorption column. The stream (13) of material is cooled to 65° C., while the stream (14) of material is cooled to 30° C. Under steady-state conditions, 10 ml/h of dibutyl maleate are fed to the absorption column with the stream (10) of material.

We claim:

1. A process for the continuous separation of maleic anhydride from a gaseous reaction mixture obtained by catalytic oxidation of hydrocarbons at from 250° to 600° C., by treatment of the gaseous reaction mixture with a solvent, wherein the gaseous reaction mixture which contains maleic anhydride and has been cooled to 50°–200° C. and from 0.2 to 10 moles of butanol per mole of maleic anhydride are fed into the lower part of a column, water is removed from the column above this feed point, from 0.2 to 20 moles of dibutyl maleate per mole of maleic anhydride are fed in via the top of the column, and the liquid product containing butyl maleate is removed from the bottom of the column.

2. A process as claimed in claim 1, wherein liquid mixture is removed from the middle part of the column, fractions which are lower boiling than dibutyl maleate are distilled off from this mixture and fed into the lower part of the column, and the butyl maleate obtained as a bottom product in this distillation is fed in via the top of the column.

* * * * *